United States Patent

Bell

Patent Number: 4,546,500
Date of Patent: * Oct. 15, 1985

[54] FABRICATION OF LIVING BLOOD VESSELS AND GLANDULAR TISSUES

[75] Inventor: Eugene Bell, Dedham, Mass.

[73] Assignee: Massachusetts Institute of Technology, Cambridge, Mass.

[ * ] Notice: The portion of the term of this patent subsequent to Sep. 10, 2002 has been disclaimed.

[21] Appl. No.: 352,585

[22] Filed: Feb. 26, 1982

Related U.S. Application Data

[63] Continuation-in-part of Ser. No. 261,928, May 8, 1981, Pat. No. 4,539,716.

[51] Int. Cl.[4] .............................................. A61F 1/00
[52] U.S. Cl. ........................................ 623/1; 128/1 R; 435/1; 623/2; 623/12; 623/14
[58] Field of Search .................. 3/1, 1.4; 435/240–241, 435/1; 128/DIG. 8

[56] References Cited

U.S. PATENT DOCUMENTS

| | | | |
|---|---|---|---|
| 3,425,418 | 2/1969 | Chvapil et al. | 3/1.4 X |
| 3,883,393 | 5/1975 | Knazek et al. | 435/240 |
| 3,910,819 | 11/1975 | Rembaum et al. | 435/240 |
| 3,949,073 | 4/1976 | Daniels et al. | 3/1.9 X |
| 4,060,081 | 11/1977 | Yannas et al. | 128/DIG. 8 |
| 4,319,363 | 3/1982 | Ketharanathan | 3/1.4 |

OTHER PUBLICATIONS

Sarber, R. et al., "Regulation of Proliferation of Fibroblasts of Low and High Population Doubling Levels Grown in Collagen Lattices", *Mech. Ageing & Dev.* 17, 107–117 (1981).

Bell, Eugene et al., "Development and Use of a Living Skin Equivalent", *J. Plastic & Reconstructive Surgery* 67, 386–392 (1981).

Elsdale et al., J. Cell. Bio., vol. 54 (1972), pp. 626–637.

Ehrmann et al., J. Nat'l. Canc. Inst., vol. 16 (1956), pp. 1375–1403.

Michalopoulos et al., Experm. Cell. Res., vol. 94 (1975), pp. 70–78.

*Primary Examiner*—Richard J. Apley
*Assistant Examiner*—David J. Isabelle
*Attorney, Agent, or Firm*—Arthur A. Smith, Jr.; David E. Brook; Leo R. Reynolds

[57] ABSTRACT

A method and apparatus for producing a vessel-equivalent prosthesis is described. A contractile agent such as fibroblast cells, smooth muscle cells or platelets is incorporated into a collagen lattice and contracts the lattice axially around an inner core. After the structure has set, additional layers may be formed in an ordered manner depending on the intended function of the prosthesis. Alternatively, all the layers may be formed concurrently. A plastic mesh sleeve is sandwiched between layers or embedded within the smooth muscle cell layer to reinforce the structure and provide sufficient elasticity to withstand intravascular pressure.

16 Claims, 4 Drawing Figures

FABRICATION OF LIVING BLOOD VESSELS AND GLANDULAR TISSUES

RELATED APPLICATION

This application is a continuation-in-part of Ser. No. 261,928 filed May 8, 1981, now U.S. Pat. No. 4,539,716 and is related to Ser. No. 972,832 filed Dec. 26, 1978 and Ser. No. 245,536 filed Mar. 19, 1981, both of which are now abandoned in favor of continuation-in-part applications.

TECHNICAL FIELD

This invention is in the field of biology and particularly relates to the fabrication of living tissue in tubular form for various applications such as capillaries, larger blood vessels and glandular prosthesis.

BACKGROUND ART

Some of the material in the first of the referenced related applications above has been published in the *Proc. Natl. Acad. Sci. USA* Vol. 76 No. 3 pp 1274–1278 March 79 in an article entitled "Production of a Tissue-Like Structure by Contraction of Collagen Lattices by Human Fibroblasts of Different Proliferative Potential In Vitro" by Bell et al. This article and the related applications are mainly concerned by the fabrication of planar surfaces of skin-like living tissue. This living tissue is produced in vitro by forming a hydrated collagen lattice, containing a contractile agent, such as fibroblast cells or blood platelets which contract the lattice. This skin-like tissue is formed in a round or rectangular vessel with, or without, a frame of stainless steel mesh lying on the floor of the vessel. In its absence, the lattice contracts in all dimensions; in its presence as the lattice sets it becomes anchored to the mesh and contracts in the thickness dimension only. The mesh, resembling a picture frame, holds the lattice of living tissue within it. The contracted lattice, with or without the stainless steel mesh frame, can be seeded with epidermal cells from the potential graft recipient. When a sheet of epidermal cells forms, the two layered skin equivalent is grafted.

The resultant graft is unique as compared to any other graft obtained from artificial skin since its basic organization is like that of skin and its living constituent cells are donated by potential graft recipients.

DISCLOSURE OF THE INVENTION

This invention relates to the casting of living collagen lattices contracted by living cells, such as fibroblasts, smooth muscle cells, or elements of cells such as blood platelets. In particular, the lattices are cast into shapes which provide internal surface areas and tubular shaped terminals, or end structures, particularly effective for making connections, in vivo, with existing tubular structures, such as capillaries, blood vessels and glandular tissues.

The internal surface of the cast structure is lined with specialized cells, depending on the function of the structure. For example, endothelial cells are used for the internal surface of an artery, vein, or other structures with internal surfaces.

Alternatively, in some applications it may be desirable to line the internal surface with specialized cells having a predetermined therapeutic value. For example, the inner surfaces of a capillary bed may be lined with pancreatic $\beta$ cells to boost the insulin supply in the blood. Pancreatic islets (islets of Langerhans), hepatocytes or other types of glandular cells may also be used for lining the inner surface of the vessel-equivalent structures.

In one embodiment, the structure is in the form of a tube, or cylinder. The central core for forming the tube consists of polyethelene or glass tubing. This core is axially centered within a cylindrical mold. Suitable tissue forming constituents are poured into the cylindrical mold. After a suitable period of time, the tissue forming constituents contract the lattice and close in around the central core. This procedure can be repeated as many times as desired with the same or different cell types in the same or different proportions to yield a multilayer tube. After each layer contracts the fluid expressed from the contracting lattice is poured off to accomodate the tissue forming constituents of the next layer. The central core may then be removed and suitable cells, predicated on the function of the cast structure, may then be cultured on the inner surface of the hollow tissue cylinders, to form, for example, a vessel-equivalent structure.

The fortuitous fact that the lattice contracts radially about the central core structure to form tubes enables one to form various shaped structures defined by the inner core surface. If, instead, the lattice contracted in all directions, the resultant structure would end up as a shapeless mass at the bottom of the mold. It is also important to note that in the formation of vessel-equivalent structure, in accordance with the invention, the sequential addition of cells in an ordered pattern of layers is essential.

The vessel-equivalent structure thus far described is devoid of elastin, the fibrous mucoprotein which is the major connective tissue protein of elastic structures (e.g. large blood vessels). Without this elastic property it is possible that the vessel could burst under pressure. Since elastin is an extremely insoluble substance it is difficult to directly incorporate elastin into the molded tissue forming constituents previously described. Accordingly, a plastic mesh may be optionally provided between two layers or within a layer of the tissue forming constituents during the molding process, as will be described in detail.

This mesh serves to reinforce the resultant vessel and at the same time provide a degree of elasticity to the structure so that it may expand and contract in the manner of a natural blood vessel having elastin.

BEST MODE OF CARRYING OUT THE INVENTION

The following description generally relates to the casting of cylindrical structures intended as prosthesis for vessels or capillaries since such structures are commonly found in the human body. However, other shapes may be conviently cast in accordance with the teachings herein and the invention is not intended to be limited to any particular shape or body structure.

Figures 1, 1A, 1B:
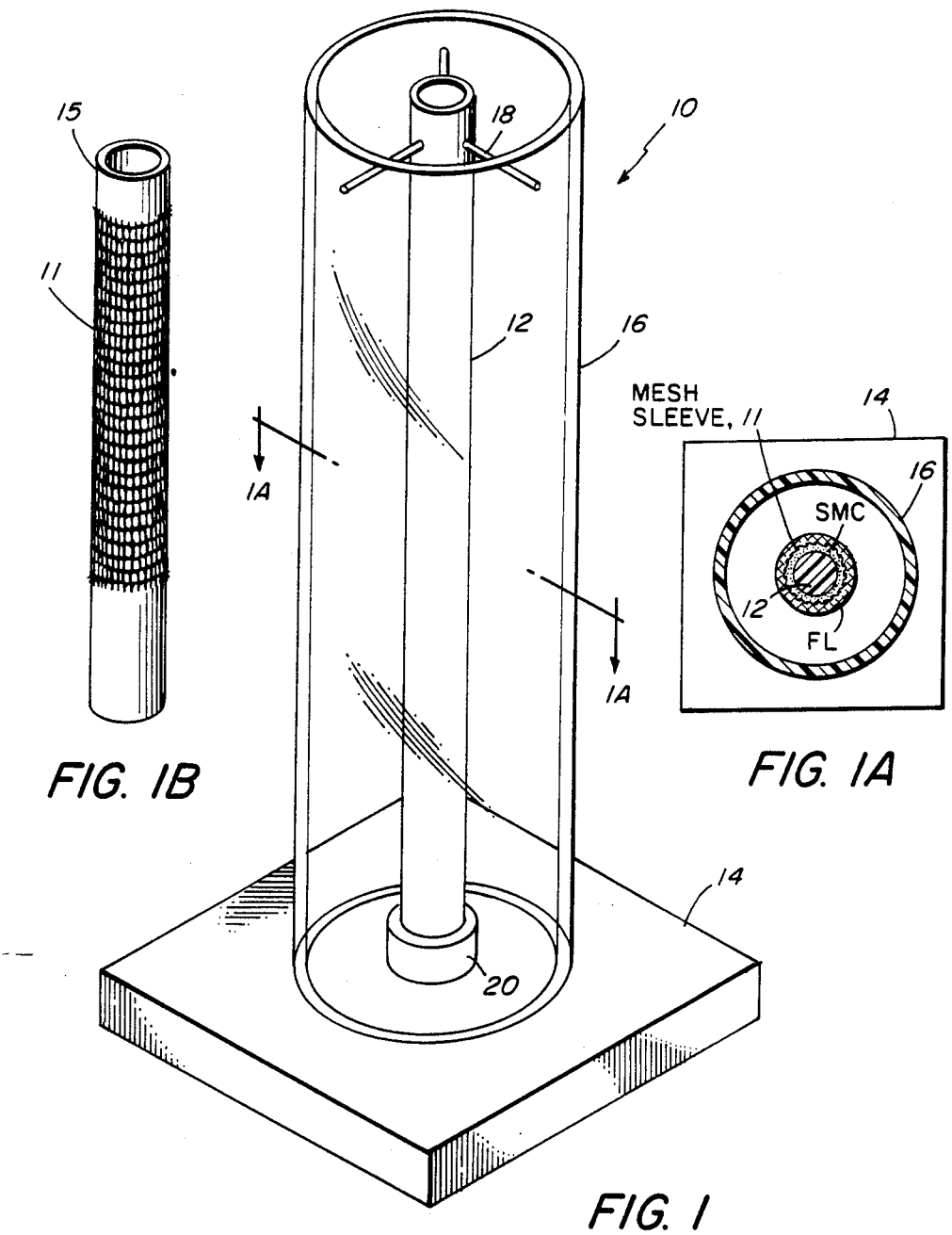
FIG. 1 is a perspective view of a first embodiment of the invention showing the structure of the casting chamber.
FIG. 1A is a cross-sectional view of FIG. 1 showing a vessel as cast.
FIG. 1B is a perspective view showing a plastic mesh on a support tube which is used to position the mesh during casting.

FIG. 1 shows a preferred form of casting chamber for fabricating a blood vessel-equivalent of living matter. The casting chamber 10 comprises a central rod or mandrel 12 disposed in a cylinder 16. The central rod and cylinder are mounted on a base or stand 14. The rod 12 is provided with three arms or spokes 18 at the top of the rod for centering the rod within the cylinder 16.

The base is provided with an appropriate collar 20 to accept the central rod 12. The outer cylinder has an internal diameter such that when the arms 18 are disposed as shown and the central rod is located in the collar 20, the rod 12 will be centered within cylinder 16. The outer diameter of the rod 12 determines the inner diameter of the cast vessel and for many applications would be in the range of from 2–10 mm.

With the diameter of the central rod kept constant, the inner diameter of cylinder 16 will determine the final thickness of the cast layer, and typically may range from 1–4 cm to produce a final thickness of about 0.5–2 mm, the final thickness being proportional to the diameter. The height of the chamber determines the length of the vessel and would typically be between 10–30 cm in height.

The casting chamber parts should be made from material which may be readily cleaned and is autoclavable. Preferably, the cylinder 16 should be made from material which is clear and which will permit diffusion of carbon dioxide and other gases. Thus, the rod 12 may be made of glass or metal and the cylinder 16 should preferably be made of autoclavable plastic, such as polycarbonate. The stand 14 may be made of glass, plastic or metal, such as stainless steel.

The size and structure of blood vessels varies in accordance with the function of the particular blood vessel. Blood vessels may be generally characterized by their cellular composition and the composition of the matrix or collagen lattice with which other extracellular elements, such as elastin fibers and proteoglycans are associated. The collagen, elastin, and proteoglycans are the biosynthetic products of the cells in each of the layers.

The cell types are endothelial, smooth muscle, and fibroblasts (called pericytes) and are found respectively in successive layers from the lumen outward. In order to construct a particular type of blood vessel, the respective layers may be laid down in order. Alternatively, several can be laid down concurrently. All vessels contain an inner endothelial lining. In an artery, for example, smooth muscle surrounds the endothelium and the final outside layer is made up of fibroblasts.

The process for fabricating the above described multilayered blood vessel-equivalent will now be described in detail in connection with FIGS. 1 and 2.

First, the smooth muscle layer is fabricated. A mixture of nutrient medium (e.g. McCoy's medium containing fetal bovine serum) is prepared in a flask. The ingredients are mixed in the following ratio: 9.2 ml of 1.76×concentrate of McCoy's medium and 1.8 ml of fetal bovine serum. The pH is raised by addition of 1.0 ml of 0.1N NaOH. The foregoing mixture of medium and serum is poured onto a dish in which 1.5 ml of native collagen in a 1–1000 acidic acid solution has been prepared. About 250,000 cultured aorta smooth muscle cells suspended in a 0.5 ml of McCoy's medium supplemented with a 10% fetal bovine serum is quickly added.

The above constituents are mixed by swirling the dish and quickly pouring the mixture into the casting chamber. The chamber is then placed in a humidified 5% $CO_2$, 95% air incubator at 37° C. for 3 days.

A collagen lattice or gel forms immediately on casting the mixture. The collagen fibrils are gradually compacted by the cells so that fluid is squeezed out of the lattice. The result is contraction of the collagen lattice around the central core or rod 12. After 3 days in the incubator, the smooth muscle layer will have set in a cylindrical structure having sufficient structural integrity to simulate, or replicate, the smooth muscle layer of a typical blood vessel. If a second layer is to be applied, the fluid expressed during contraction of the first lattice is poured off and a second complete mixture of all ingredients is added to replace the fluid. The process may be repeated as many times as desired to give a multilayered structure. The layers may be poured simultaneously with a removable separation or sleeve (not shown) between them. As soon as gelation begins the sleeve is removed.

Optionally, after the smooth muscle layer cylinder has been cast, it may be desirable to provide a plastic mesh sleeve 11 about the outer surface of the smooth muscle layer cylinder or the mesh may be embedded in the smooth muscle layer. This mesh will serve to reinforce the resulting structure and provide some degree of elasticity so that the resulting structure will be better able to withstand the pressures it will be subjected to in use. Meadox Medicals, Inc., 103 Bauer Drive, Oaklane, N.J. 07436, supplies a Dacron ® mesh sleeve, Part No. 01H183, which has proved particularly suitable for this purpose. Other suitable meshes are readily available in various inert plastics, such as Teflon ®, nylon, etc. and the invention is not to be limited to a particular plastic material. Preferably, the mesh should be treated to render it more electronegative by, for example, subjecting it to plasma. This results in better cell attachment to the plastic sleeve and hence an increase in the strength of the resultant structure.

The sleeve 11 should be placed on the smooth muscle cell cylinder by first disposing the sleeve 11 on metal tube 15 (as shown in FIG. 1B) which has an inner diameter larger than the outer diameter of the smooth muscle cell cylinder. The tube 15, with the sleeve on the exterior, is then slipped over the smooth muscle cell cylinder, a portion of the sleeve is then pulled off the tube 15 and onto the smooth muscle cell cylinder and held there while the tube 15 is slipped off the smooth muscle cell cylinder. This procedure minimizes damage to the exterior surfaces of the smooth muscle cell cylinder while attaching the sleeve.

Next, a fibroblast layer may be cast around the inner smooth muscle layer(s) and sleeve 11 so as to completely enclose the sleeve 11, as shown in FIG. 1A. In this process, the ingredients described above in connection with the fabrication of a smooth muscle layer are used to constitute a fibroblast layer, except that cultured aorta fibroblasts are substituted for the smooth muscle cells. The incubation period for the fibroblast layer may be 2 days to a week.

The resultant multi-layered structure consisting of inner smooth muscle layer(s) and an outer fibroblast layer with a mesh sleeve sandwiched between the two layers is now ready to be cultured with an inner endothelial lining of living endothelial cells. To perform this step the cylindrical tissue tube of several layers is slipped off the casting rod 12 to receive the endothelial cells as a suspension. It is supported in the culturing apparatus shown in FIG. 2.

Figure 2:
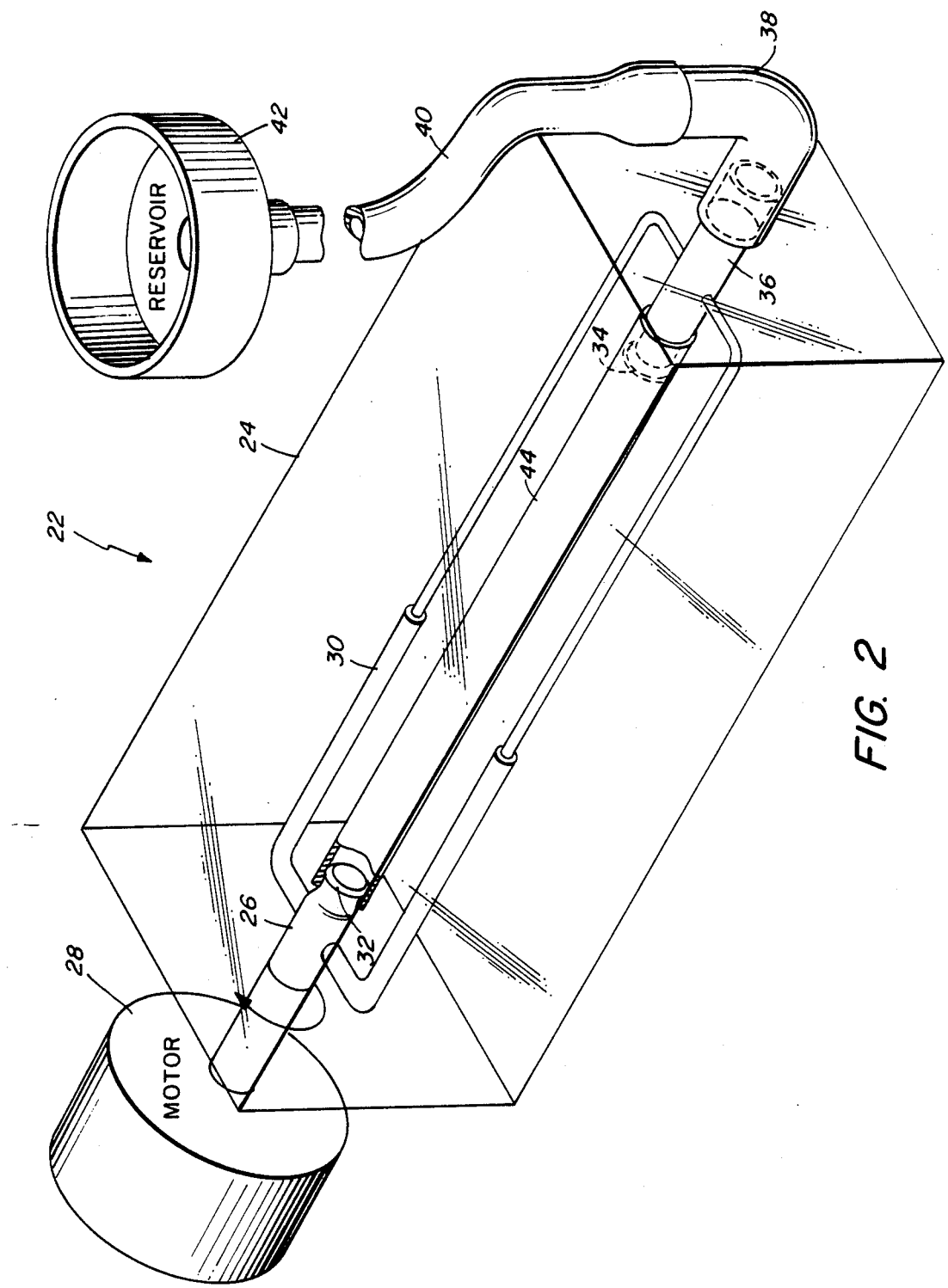
FIG. 2 is a schematicized view showing the culturing apparatus of the invention.

The apparatus of FIG. 2 comprises a transparent chamber 24, within which a rotatable rod 26 is inserted at one end and a rotatable tube 36 is inserted at the opposite end. The tube 36 and rod 26 are tied together by wire frame member 30 such that when the rod 26 is rotated, the tube 36 will rotate in unison in the same direction. Rod 26 is coupled to motor 28 such that when motor 28 is energized the rod 26 will rotate in the direction shown by the arrow. Preferably, the rod is attached to the motor in such a way that the length of the rod inserted into the chamber 24 may be adjusted in accordance with the length of the vessel-equivalent 44 being supported within the culture chamber 24. This may be accomplished by a rack and pinion device or other such variable length means (not shown).

Rod 26 is provided at one end with a nipple 32 to which a vessel 44 (such as the structure previously described in connection with FIGS. 1, 1A and 1B comprising an inner cylinder smooth muscle cell layer, and an outer cylinder of fibroblast cells with a mesh sleeve sandwiched between) may be attached. Similarly, tube 36 is provided with a complementary nipple 34 to which the opposite end of the vessel 44 may be attached. In this manner, the vessel 44 is suspended between the rod 26 and tube 36 and a culture medium may be introduced from reservoir 42 through tubing 40 and fixed connecting tube 38, through tube 36 and into the interior lining of blood vessel-equivalent 44. It should be understood that water-tight seal bearings (not shown) are provided at both ends of chamber 24 to permit the rod and tube to be inserted into the chamber.

Reservoir 42 is supplied with a suspension of about 200,000 cultured aorta or other endothelial cells in McCoy's medium supplemented with a 20% fetal bovine serum. This mixture is fed by hydrostatic pressure from the reservoir into the vessel 44 as previously mentioned. Next, the vessel 44 is slowly rotated by means of motor 28 which preferably runs at a speed of between 0.1 and 1 r.p.m. Rotation of the vessel 44 enables distribution of the endothelial cells evenly on the inner lining of the vessel and the hydrostatic pressure head from the reservoir enables the lumen, or inner opening, of the vessel-equivalent to remain open. It should be emphasized that the above procedures are intended to be carried out asceptically.

EQUIVALENTS

Those skilled in the art will recognize or be able to ascertain, using no more than routine experimentation, other equivalents for the specific reactants, steps and techniques, etc. described herein. Such equivalents are intended to be included within the scope of the following claims.

I claim:

1. In a method of producing, in vitro, a living multi-layered tubular structure, comprising:
    a. producing a first tubular layer by:
        (1) forming a first aqueous mixture of collagen fibrils, nutrient medium and a first cellular contractile agent capable of interacting with collagen fibrils;
        (2) introducing said first mixture into an annular casting chamber;
        (3) maintaining the annular casting chamber containing said first mixture under conditions sufficient to allow a gel to form therein and to allow radial contraction of the gel with expression of aqueous liquid therefrom resulting from interaction of the cellular contractile agent with collagen fibrils to thereby form a contracted hydrated collagen lattice suitable as one layer of a multi-layered tubular structure; and
        (4) removing aqueous liquid expressed in the formation of said first tubular layer from the annular casting chamber;
    b. producing a second tubular layer outwardly of said first tubular layer by:
        (1) forming a second aqueous mixture of collagen fibrils, nutrient medium and a second cellular contractile agent capable of interacting with collagen fibrils;
        (2) introducing said second mixture into the annular casting chamber;
        (3) maintaining the annular casting chamber containing said second mixture under conditions sufficient to allow a gel to form therein and to allow radial contraction of the gel with expression of aqueous liquid therefrom resulting from interaction of the cellular contractile agent with collagen fibrils to thereby form a contracted hydrated collagen lattice suitable as another layer of a multi-layered tubular structure; and
    c. removing said multi-layered tubular structure from the annular casting chamber;
    The improvement comprising adding a reinforcing sleeve of inert material to said living multi-layered tubular structure.

2. The improvement of claim 1 wherein said reinforcing sleeve of inert material comprises a plastic mesh sleeve.

3. The improvement of claim 2 wherein said plastic mesh sleeve is located between the first and second tubular layers of the living multi-layered tubular structure.

4. The improvement of claim 3 wherein the plastic mesh sleeve is attached by first slipping it on a tube and subsequently sliding the tube over the first tubular structure and removing the tube leaving the sleeve positioned over the first tubular structure.

5. The improvement of claim 3 wherein said plastic mesh sleeve is pretreated to render it more electronegative.

6. The improvement of claim 5 wherein said plastic mesh screen is pretreated by subjecting it to plasma.

7. A living multi-layered tubular structure produced by the improvement of claim 1.

8. A living multi-layered tubular structure produced by the improvement of claim 3.

9. In a method of producing a living prosthesis, in vitro, comprising the steps of:
    a. fabricating a cylindrical smooth muscle cell layer as follows:
        (aa) separately preparing (i) an aqueous acidic mixture comprising nutrient medium and collagen fibrils and (ii) a mixture of smooth muscle cells suspended in nutrient medium;
        (ab) raising the pH of mixture (i) and quickly combining mixture (i) and mixture (ii) and pouring the combined mixture into a casting chamber having an inner core member and an outer cylindrical wall structure to form a lattice;
        (ac) incubating the lattice for a period sufficient to enable collagen fibrils to be compacted by the cells so that aqueous liquid is expressed out of the lattice as the lattice contracts radially about the core;

(ad) removing aqueous liquid expressed in step (ac);

(ae) repeating steps (aa)–(ad) if additional layers of smooth muscle cells are desired;

b. fabricating a layer containing fibroblast cells on said cylindrical smooth muscle layer as follows:

(ba) separately preparing (i) an aqueous acidic mixture comprising nutrient medium and collagen fibrils and (ii) a mixture of fibroblast cells suspended in nutrient medium;

(bb) raising the pH of mixture (i) and quickly combining mixture (i) and mixture (ii) and pouring the combined mixture into a casting chamber having as an inner core member of cylindrical smooth muscle cell layer and an outer cylindrical wall structure to form a lattice;

(bc) incubating the lattice formed in step (bb) in accordance with step (ac);

(bd) removing aqueous liquid expressed in step (bc);

c. lining the inner wall of the cylindrical smooth muscle cell layer with living cells;

The improvement of including a plastic mesh within said living prosthesis to thereby reinforce said living prosthesis and to provide it with an increased degree of elasticity.

10. The improvement of claim 8 wherein said plastic mesh comprises a sleeve positioned between the layers of smooth muscle cells and fibroblast cells.

11. The improvement of claim 10 wherein said plastic mesh screen comprises polyethylene terephthalate.

12. The improvement of claim 11 wherein said plastic mesh screen is pretreated to make it more electronegative.

13. The improvement of claim 12 wherein said pretreatment is done by exposing the plastic mesh screen to plasma.

14. A living multi-layered tubular structure produced by the improvment of claim 9.

15. In a tubular prosthesis formed of multiple layers of hydrated collagen lattices contracted with living cells:

The improvement comprising including a plastic mesh sleeve embedded in the layers of said prosthesis to provide reinforcement and elasticity thereto.

16. The improvement of claim 15 wherein said plastic mesh sleeve is formed from polyethylene teraphthalate.

* * * * *